United States Patent [19]
Parks

[11] Patent Number: 4,701,163
[45] Date of Patent: Oct. 20, 1987

[54] GASTROSTOMY FEEDING DEVICE

[75] Inventor: Stephen K. Parks, Sunnyvale, Calif.

[73] Assignee: Medical Innovations Corporation, Milpitas, Calif.

[21] Appl. No.: 670,381

[22] Filed: Nov. 5, 1984

[51] Int. Cl.⁴ .............................................. A61M 25/00
[52] U.S. Cl. ..................................................... 604/178
[58] Field of Search .................. 604/97, 96, 104, 174, 604/175, 178, 180, 280; 128/DIG. 26

[56] References Cited

U.S. PATENT DOCUMENTS 4,543,089 9/1985 Moss ..................................... 604/93

OTHER PUBLICATIONS

Gerald Moss, "Efficient Gastroduodenal Decompression with Full Enteral Nutriton: A New Gastrostomy Catheter Technique", *Journal of Parenteral and Enteral Nutrition*, vol. 8, No. 2, 3/14/84, pp. 203–207.

*Primary Examiner*—Stephen C. Pellegrino
*Attorney, Agent, or Firm*—Willie Krawitz

[57] ABSTRACT

A device is disclosed for supplying food and medication to a patient, the device being inserted through a stoma and into the patient's stomach.

The device is secured within the stomach by an inflatable balloon, and on the abdominal wall by an adjustable ring which also prevents ingestion of the device into the stomach. During use, the adjustable ring can be retracted to permit cleaning of the stoma area.

The device can be employed with conventional surgically formed procedures, and is replaceable at considerably longer intervals than present devices. Servicing of the device can be made at home, rather than at a hospital.

14 Claims, 4 Drawing Figures

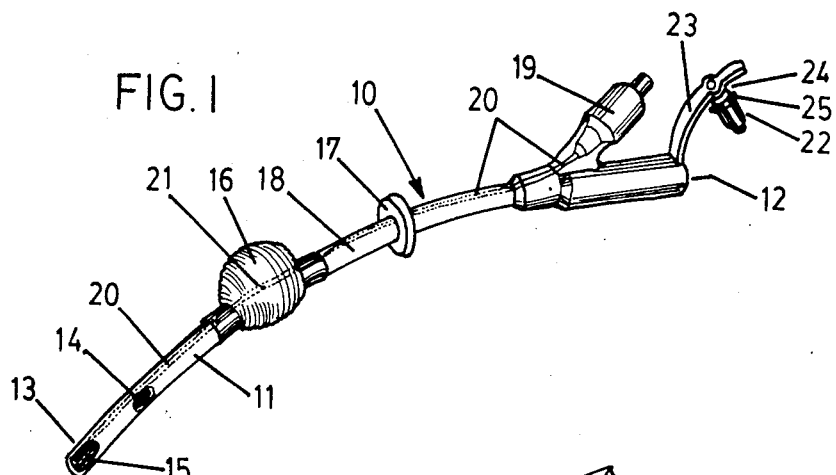
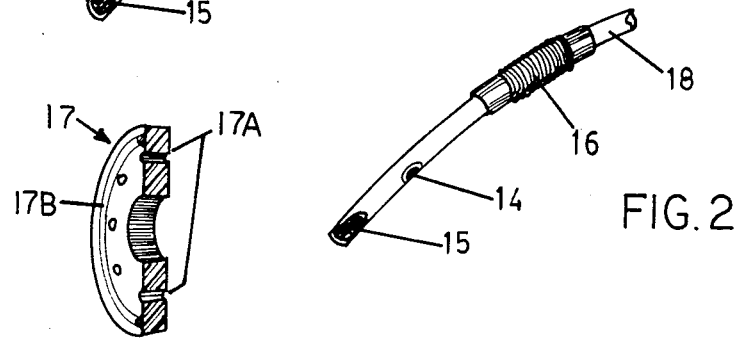
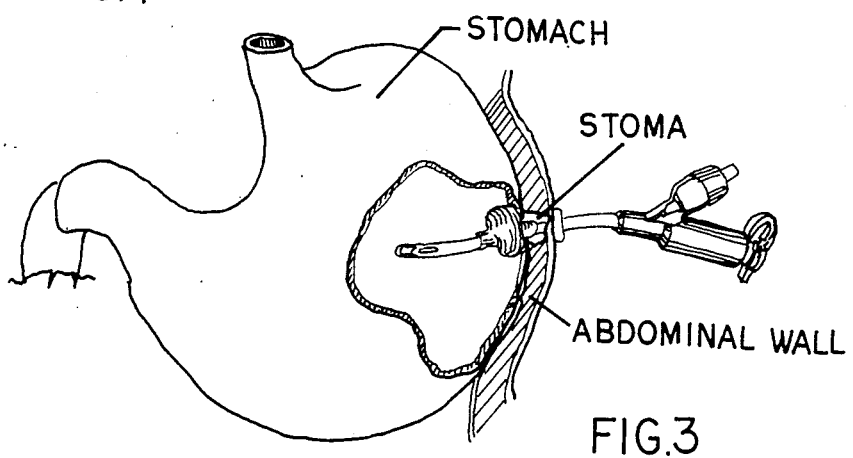

GASTROSTOMY FEEDING DEVICE

BACKGROUND OF THE INVENTION

This invention relates to a new and improved feeding tube, and more specifically to a gastrostomy feeding tube that is insertable through a stoma in the patient's stomach wall and secured within the patient's stomach.

Many types of feeding devices have been developed, but they suffer from various drawbacks. These include: the ejection or loss of liquids from the stomach and back out through the device; leaking around the periphery of the device; and, premature deterioration of the materials of construction. Also, it is difficult to maintain the device in place in a stable manner in the patient, and this latter problem can result in the device being ingested into the stomach, and eventually into the pylorum. Devices presently on the market are not sized properly, and they use materials that are prone to fairly rapid deterioration. Moreover, they can become entangled and dislodged from the patient due to improper sizing and inadequate locking of the device to the patient. In some prior art devices, the exterior of the gastrostomy tube is taped to the wearer's body, and this can cause infection at the stoma entry, and along the taped area, as well as causing irritation due to the difficulty in maintaining these areas clean.

THE INVENTION

According to the invention, a gastrostomy feeding tube is provided for insertion through the stoma of the patient's stomach wall and into the patient's stomach. The gastrostomy tube is provided with an inflatable tube at one end to position and secure the tube within the stomach. The outer end of the tube is provided with a moveable locking ring that can be adjusted to accommodate to the size of the wearer. Since the locking ring does not require or employ tape to secure the device in place, problems associated with skin irritation and with maintaining both the taped areas and the stoma area clean, are greatly reduced. The locking ring can simply be moved along the tube to permit cleaning of the stoma entry through which the catheter is inserted. The locking ring is then repositioned to its normal location, i.e. in close contact with the wearer's abdomen. The balloon and locking ring thus both function to maintain the device in place, and prevent the device from being drawn into the stomach, or inadvertently pulled out.

The device of this invention is preferably manufactured of a medical grade silicone elastomer, rather than a latex or silicone latex combination. Consequently, use of the silicone elastomer provides a relatively inert material compared to the latex. Accordingly, the elastomer requires replacement about every 6-8 weeks compared to the silicone latex which needs replacement about every 3 weeks.

BRIEF DESCRIPTION OF THE DRAWINGS:

FIG. 1 is an external perspective view of the gastrostomy device of this invention;

FIG. 2 is an external perspective view of the said device, fragmented, showing the outlet end, and the balloon when deflated;

FIG. 3 is a perspective view, partly broken away, of the said device installed in a patient; and, FIG. 4 is an external perspective view of a preferred form of locking ring employed in the device.

DESCRIPTION OF THE PREFERRED EMBODIMENTS

The gastrostomy catheter device 10 of this invention is shown in FIG. 1, and provides an inlet end 12, through which is fed food and medication, and an outlet end 13 that extends into the patient's stomach. A plurality of outlet ports, two of which ports 14, 15 are shown, and located at the outlet end 13. The catheter 10 is secured inside the stomach by an inflatable balloon 16, and on the patient's abdomen by an adjustable silicone locking ring 17. As shown in FIG. 4, the locking ring 17 is provided with a plurality of vent holes 17A to permit air to contact the entry to the stoma and reduce infection and skin irritation. A circular ridge 17B is formed on the locking ring also improves air circulation between the ring and the patient's abdomen.

As indicated, use of the ring prevents the catheter from being drawn into the patient's stomach. In addition, since the adjustable ring does not require the use of tape, a potential source of skin irritation and infection is eliminated. The portion 18 of the catheter tube 11 between the ring 17 and balloon 16 is secured within the stoma, and this arrangement of the balloon and ring prevents the catheter from being drawn into the patient's stomach.

In FIG. 1, the balloon is inflated by liquid or gas which is passed through a valve 19 and line 20 into a port 21 that is surrounded by the balloon. The line 20 is bonded along the inside of the catheter tube 11 and extends to the outlet of the catheter where it is end sealed; the end seal forces the inflating gas into the port 21. FIG. 2 shows the balloon 16 in a deflated position.

The inlet end 12 is provided with an integrally formed end plug 22 attached to the catheter by a band 23. A plurality of rings 24, 25 arc formed on the plug to engage corresponding grooves (not shown) on the inside of the bore at the inlet. The combined effect of the plug and bore fit, and the fit between the grooves and rings prevent the plug from being dislodged during use, and hence, will prevent the contents of the stomach from draining out the catheter.

Basically, the catheter device is inserted into the patient through a surgically prepared stoma created in the abdominal wall using pre-existing surgical procedures. These procedures include Stamms Gastrostomy, Witzel Gastrostomy, and others. Also, non surgical procedures may be employed such as percutaneous gastrostomy. The catheter tube 10, with surrounding, concentric purse string sutures, is inserted through the stoma and gastric wall into the stomach. The purse strings will permanently invaginate a portion of the stomach and stoma to shape around the catheter tube and then will dissolve, leaving the gastrostomy tube in place and ready for use. FIG. 3 shows the device when installed. The inflated balloon forms a gasket that seals the entrance to the stoma, and along with the locking ring 17, secures the device in place. The device may be constructed in various sizes to accommodate a particular patient. Sizes such as 12, 14, 16, 18 and 20 French, and corresponding diameters varying from about 0.157"-0.263", and a wall thickness of about 0.035", may be employed.

After being used for a suitable time, say 6-8 weeks, the catheter tube is, of course, replaced. This is accomplished simply by deflating the balloon, retracting the adjustable ring, and removing the tube from the patient.

The present device is inexpensive and can be readily manufactured by conventional extrusion and injection molding techniques. Also, it can be easily inserted for use without generally requiring the services of a physician or even out-patient services.

The device may be cleaned during use and can be manipulated to permit cleaning of the stoma area. Finally, the device is safe in that it cannot be drawn into the stomach, which can be particularly dangerous to unsuspecting infants. During use, it will not inadvertantly drain the contents of the stomach, because of the end plug.

I claim:

1. A gastrostomy catheter device for feeding into a patient's stomach, comprising:
   a. an elongate feeding tube having a feeding inlet end and a perforated outlet end for discharging food, the feeding tube extending outwardly from the patient's stomach to support external components of the device;
   b. an inflatable balloon structure mounted around the tube and positioned near the outlet end of the tube;
   c. an inflation valve mounted near the inlet end of the tube;
   d. a valve line connected to the valve and providing an outlet port within the balloon structure, the valve line being positioned adjacent the feeding tube;
   e. a closure plug for the feeding inlet and secured to the feeding tube by an integral band and to prevent stomach drainage;
   f. a perforated, adjustable ring slidably mounted along the feeding tube, and medially thereof, and sized to frictionally engage the tube; whereby
      i. when the balloon is deflated, the feeding tube may be inserted through a stoma and into the patient's stomach;
      ii. when the balloon is inflated through the valve and valve line, it is adapted to form a seal within the patient's stomach and adjacent the stoma;
      iii. securement of the ring to the tube being provided solely by frictional engagement therebetween, the ring and tube both being made of silicone material, or the like, to secure the device within the patient's body and to prevent undesirable movement of the ring along the tube, whether in the dry state or when lubricated by body fluids, the locking ring being manually adjustable along the tube to accommodate to the size of the patient, and the balloon and ring both functioning to maintain the device in place in the patient;
      iv. retraction of the ring along the feeding tube away from the patient's body being entirely against frictional engagement forces between the ring and tube to enable the stoma and adjacent areas to be cleaned; and,
      v. when the balloon is deflated, retraction of the ring along the feeding tube enables the device to be removed from the patient.

2. The catheter of claim 1, in which the adjustable ring is perforated to admit air to the stoma.

3. The catheter of claim 2, in which the adjustable ring provides a ridge on one side thereof, to increase air circulation between the ring and stoma.

4. The catheter of claim 1, in which the device is constructed of a medical grade silicone elastomer.

5. The catheter of claim 4, having a stability time in the patient of at least about 6 weeks.

6. The catheter of claim 1, in which the valve line is formed integrally with the feeding tube.

7. The device of claim 1, comprising a closure plug and bore fit at the feeding inlet to prevent drainage from the stomach through the catheter.

8. A method for gastrostomy feeding, comprising
   a. inserting a gastrostomy tube through a stoma and into a patient's stomach; and,
   b. supplying food through the tube to the patient's stomach, the said tube comprising:
      i. an elongate feeding tube having a feeding inlet end, and a perforated outlet end for discharging food, the feeding tube extending outwardly from the patient's stomach to support external components of the device;
      ii. an inflatable ballon structure mounted around the tube, and positioned near the outlet end of the tube;
      iii. an inflation valve mounted near the inlet end of the tube;
      iv. a valve line connected to the valve and providing an outlet port within the ballon structure, the valve line being positioned adjacent the feeding tube;
      v. a closure plug for the feeding inlet and secured to the feeding tube by an integral band and to prevent stomach drainage;
      vi. a perforated, adjustable ring slidably mounted along the feeding tube, and medially thereof, and sized to frictionally engage the tube, whereby,
      i. when the ballon is deflated, the feeding tube may be inserted thrugh a stoma and into the patient's stomach;
      ii. when the ballon is inflated through the valve and valve line, it is adapted to form a seal within the patient's stomach, and adjacent the stoma;
      iii. adjustable movement of the ring being provided solely by frictional engagement between the ring and tube made of silicone material, or the like, to secure the device within the patient's body and to prevent undesirable movement of the ring along the tube, whether in the dry state or when lubricated by body fluids, the locking ring being manually adjustable along the tube to accommodate to the size of the patient, and the balloon and ring both functioning to maintain the device in place in the patient;
      iv. retraction of the ring along the feeding tube away from the patient's body being entirely against frictional engagement forces between the ring and tube to enable the stoma and adjacent areas to be cleaned; and,
      v. when the balloon is deflated, retraction of the ring along the feeding tube enables the device to be removed from the patient.

9. The method of claim 8, comprising perforating the adjustable ring and admitting air to the stoma through the ring perforations.

10. The method of claim 9, comprising providing a ridge on one side of the ring to increase air circulation between the ring and the stoma.

11. The method of claim 8, comprising constructing the device of a medical grade silicone elastomer.

12. The method of claim 12, comprising forming the valve line integrally with the feeding tube.

13. the method of claim 11, which comprises placig the device in the patient for at least about 6 weeks.

14. The method of claim 8, comprising preventing drainage from the stomach through the catheter by providing a bore fit between the closure plug and feeding inlet.

* * * * *